United States Patent [19]

Izumi et al.

[11] Patent Number: 5,254,684

[45] Date of Patent: Oct. 19, 1993

[54] PROCESS FOR PRODUCING AMIDE BY LIQUID PHASE REARRANGEMENT OF OXIME

[75] Inventors: Yusuke Izumi, 907 Hara-4-chome, Tenpaku-ku, Nagoya-shi; Hiroshi Sato; Hiroshi Yoshioka, both of Niihama; Yoshisaburou Nomura, Ehime, all of Japan

[73] Assignees: Sumitomo Chemical Company, Limited, Osaka; Yusuke Izumi, Nagaoya, both of Japan

[21] Appl. No.: 885,604

[22] Filed: May 19, 1992

[30] Foreign Application Priority Data

May 21, 1991 [JP] Japan .................. 3-116077
Oct. 15, 1991 [JP] Japan .................. 3-266041

[51] Int. Cl.$^5$ ............... C07D 201/04; C07D 223/00; C07D 239/00
[52] U.S. Cl. ................... 540/535; 564/215; 564/216; 564/218
[58] Field of Search ........... 564/215, 123, 216, 218; 540/535, 533

[56] References Cited

U.S. PATENT DOCUMENTS

| | | | |
|---|---|---|---|
| 3,609,142 | 9/1971 | Norell | 540/535 |
| 3,944,542 | 3/1976 | de Rooij et al. | 260/290.3 |
| 4,211,700 | 7/1980 | Michel et al. | 540/535 |
| 4,689,412 | 8/1987 | Rademacher et al. | 540/535 |
| 5,063,230 | 11/1991 | Pelletier et al. | 514/419 |

FOREIGN PATENT DOCUMENTS

| | | |
|---|---|---|
| 0461779 | 12/1991 | European Pat. Off. |
| 1545617 | 8/1969 | Fed. Rep. of Germany |
| 51-127090 | 4/1975 | Japan |
| 62-149665 | 7/1987 | Japan |

OTHER PUBLICATIONS

Egypt J. Chem., 16, No. 6, pp. 551-553 (1973), Kira et al.: "Reaction of Acid Chloride-Amide Adducts-VIII($^1$)". A New Acid Choride-Amide Addcuct from Chlorosulphonic Acid and Dimethylformamide.
Chemistry Letters, pp. 2171-2174, 1990, Izumi: "Catalytic Bechmann Rearrangement of Oximes in Homogeneous Liquid Phase".
J. Org. Chem. vol. 36, No. 15, 1971, Kelly et al.: "The Use of Lewis Base-Sulfur Trioxide Complexes as Reagents for the Beckmann Rearrangment of Ketoximes" 2159–2161.
Patent Abstracts of Japan, vol. 4, No. 13 (C-76(713) Mar. 22, 1977 & JP-A-51 127 090 (Ube Kosan K.K.) May 11, 1976.
Journal of Organic Chemistry, vol. 38, No. 23, Nov. 16, 1973, Easton, U.S., pp. 4071-4073; Philip E. Eaton et al.: "Phosphorous pentoxide-Methanesulfonic acid. A convenient alternative to polyphosphric acid".

Primary Examiner—Allen J. Robinson
Assistant Examiner—Shailendra Kumar
Attorney, Agent, or Firm—Stevens, Davis, Miller & Mosher

[57] ABSTRACT

A process for producing an amide which comprises subjecting an oxime to liquid phase rearrangement in the presence of phosphorus pentoxide and at least one compound selected from the group consisting of N,N-dialkyl amides, N-alkyl cyclic amides and dialkyl sulfoxides and optionally a fluorine-containing strong said or its derivative. Said process can rearrange an oxime to a corresponding amide in a good yield under mild reaction conditions in the presence of a less stoichiometric amount of a catalyst.

14 Claims, No Drawings

PROCESS FOR PRODUCING AMIDE BY LIQUID PHASE REARRANGEMENT OF OXIME

This invention relates to a process for producing an amide by liquid phase rearrangement of an oxime.

Rearrangement of an oxime to an amide is known as Beckmann rearrangement. For example, in the production of $\epsilon$-caprolactam by rearrangement of cyclohexanone oxime, fuming sulfuric acid is used as a catalyst in industry. However, in processes using fuming sulfuric acid, there is an essential problem that a large amount of ammonium sulfate is produced as a by-product, and there are many other problems such as corrosion of apparatus and the like. Thus, there has been desired a development of an efficient catalyst for the rearrangement.

For example, a solid oxide catalyst in which boron oxide is supported on silica, alumina or titania and a zeolite catalyst have been proposed. However, when these solid catalysts are used in the rearrangement, it is necessary to adopt gas phase reaction at high temperatures, so that the reaction is accompanied by reduction of $\epsilon$-caprolactam yield, deterioration of catalyst and an increase of energy cost. Thus, the use of the solid catalysts has a problem in commercial production.

Some processes for producing $\epsilon$-caprolactam by rearranging cyclohexanone oxime under such relatively mild reaction conditions that liquid phase reaction is effected are known. One of the processes uses as a catalyst an ion pair obtained by reacting N,N-dimethylformamide with chlorosulfonic acid (namely, Bilsmeyer complex) [see M. A. Kira and Y. M. Shaker, Egypt, J. Chem., 16,551 (1973)] It is stated, however, that in this process, the lactam produced and the catalyst form a 1:1 complex, so that it is necessary to use the catalyst in an amount equimolar to the oxime. For this reason, said process cannot be said to be economical.

One of the present inventors previously reported liquid phase Beckmann rearrangement using a catalyst consisting of an N,N-dialkylformamide and an alkylating agent obtained from an epoxy compound and a strong acid (boron trifluoride-etherate or the like) [see Y. Izumi, Chemistry Letter, pp. 2171 et seq. (1991)]. This process is a novel, excellent rearrangement process; however, it is not always satisfactory in respect of economy and workability in its commercial application because an epoxy compound and a strong acid are required for forming an alkylating agent which is one of the rearrangement catalyst components.

Japanese Patent Application Kokai No. 62-149665 discloses a process for producing $\epsilon$-caprolactam by rearranging cyclohexanone oxime with a phosphoric acid catalyst in a heptane solvent. In this process, however, the phosphoric acid is required to be used as a catalyst in an amount as large as about 2 moles per mole of the oxime. Hence, said Japanese publication describes that the reaction mixture is neutralized with ammonia after the reaction and the phosphoric acid catalyst is recovered through complex steps and then reused.

The present inventors have made extensive research on catalysts for rearranging oximes to corresponding amides and consequently found that the oxime rearrangement is remarkably accelerated by effecting the reaction in the presence of phosphorus pentoxide and at least one compound selected from the group consisting of N,N-dialkyl amides, N-alkyl cyclic amides and dialkyl sulfoxides and optionally a fluorine-containing strong acid or its derivative.

An object of this invention is to provide a process for producing an amide free from the above-mentioned problems.

Another object of this invention is to provide a process for producing an amide by rearranging an oxime in a liquid phase at a mild reaction temperature in the presence of a catalyst in a less stoichiometric amount.

Other objects and advantages of this invention will become apparent from the following description.

According to this invention, there is provided a process for producing an amide which comprises subjecting an oxime to liquid phase rearrangement in the presence of phosphorus pentoxide and at least one compound selected from the group consisting of N,N-dialkyl amides, N-alkyl cyclic amides and dialkyl sulfoxides or in the presence of them and a fluorine-containing strong acid or its derivative.

The N,N-dialkyl amides to be used in this invention are formamides having two same or different alkyl groups having 1 to 6 carbon atoms on its nitrogen atom or $C_{1-6}$ carboxylic acid amides having two same or different alkyl groups having 1 to 6 carbon atoms on its nitrogen atom. Specific examples thereof include N,N-dimethylformamide, N,N-diethylformamide, N,N-diisopropylformamide, N,N-dibutylformamide, N,N-dihexylformamide, N,N-dimethylacetamide, N,N-diethylacetamide, N,N-diisopropylacetamide, N,N-dimethylpropionamide, N,N-dimethylbutyramide, N,N-dimethylcapronamide and the like.

The N-alkyl cyclic amides to be used in this invention are cyclic amides having 4 to 6 carbon atoms having an alkyl group having 1 to 6 carbon atoms on its nitrogen atom, and specific examples thereof include N-methylpyrrolidone, N-methylpiperidone and the like.

The dialkyl sulfoxides to be used in this invention are sulfoxides having two same or different alkyl groups having 1 to 6 carbon atoms, and specific examples thereof include dimethyl sulfoxide, diethyl sulfoxide, dipropyl sulfoxide, dihexyl sulfoxide and the like.

The rearrangement reaction activity in this invention is inhibited by water, and therefore, the above-mentioned compounds are previously dried and then used.

The fluorine-containing strong acid or its derivative includes trifluorosulfonic acids and their derivatives such as trifluoromethanesulfonic acid, trifluoromethanesulfonic acid anhydride, ethyl trifluoromethanesulfonate, trimethylsilyl trifluoromethanesulfonate, tin trifluoromethanesulfonate and the like; trifluoroacetic acid; trifluoroacetic acid anhydride; boron trifluoride; boron trifluoride-ether complex; antimony pentafluoride; and the like.

The amount of the phosphorus pentoxide used is not critical; however, it is preferably about 0.1 to 50 mole %, more preferably 1 to 20 mole %, based on the molar amount of the oxime.

The amount of the fluorine-containing strong acid or its derivative used is preferably 0.01 to 50, more preferably 0.1 to 10 moles per mole of the phosphorus pentoxide.

In this invention, the catalyst has its activity even in the absence of the fluorine-containing strong acid or its derivative; however, when the fluorine-containing strong acid or its derivative is used together with the other catalyst components, the catalyst activity can be remarkably enhanced. On the other hand, when the fluorine-containing strong acid or its derivative is used alone, only a less stoichiometric amount of oxime can be rearranged to a corresponding amide.

The process of this invention can be preferably applied to rearrangement of a ketone oxime to a corresponding amide. Specific examples of the ketone oxime include cyclohexanone oxime, cyclopentanone oxime, cyclododecanone oxime, acetone oxime, 2-butanone oxime, acetophenone oxime, benzophenone oxime and the like. Of these, cyclohexanone oxime is particularly preferably used in the process of this invention.

In this invention, the rearrangement reaction can proceed upon merely mixing phosphorus pentoxide and an oxime with at least one compound selected from the group consisting of N,N-dialkyl amides, N-alkyl cyclic amides and dialkyl sulfoxides alone or in combination with a fluorine-containing strong acid or its derivative, whereby a corresponding amide can be obtained. The process of this invention can be practised, for example, by adding phosphorus pentoxide alone or in combination with a fluorine-containing strong acid or its derivative to at least one compound selected from the group consisting of N,N-dialkyl amides, N-alkyl cyclic amides and dialkyl sulfoxides, thereafter heating the resulting mixture to the desired temperature and then dropwise adding thereto an oxime solution in an N,N-dialkyl amide or the like to subject the oxime to rearrangement.

The reaction temperature in this invention is preferably about 20°–200° C., more preferably about 30°–150° C.

After completion of the reaction, a small amount of an alkali is added to the reaction mixture to deactivate the catalyst. The reaction product is separated from the reaction mixture by a conventional means such as distillation or the like and then purified in a conventional manner.

According to the process of this invention, an oxime can be rearranged in a liquid phase under relatively mild conditions to obtain an amide in a good yield.

This invention is explained in more detail below referring to Examples which are merely by way of illustration and not by way of limitation.

In the Examples, the amide (or lactam) yield is indicated by a molar yield (%) based on the starting oxime and the selectivity is indicated by (yield/conversion)×100] (%).

EXAMPLE 1

A 200-ml, round-bottomed flask was purged with nitrogen and therein were placed 45 ml of dried N,N-dimethylformamide and 0.35 g (2.5 mM) of phosphorus pentoxide, after which the resulting mixture was heated to 60° C. Subsequently, a solution of 8.0 g (70.7 mM) of cyclohexanone oxime in 45 ml of N,N-dimethylformamide was dropwise added to the mixture at 60° C. over 60 minutes to effect reaction. After completion of the reaction, the reaction mixture was subjected to analysis by a gas chromatography to find that the conversion of cyclohexanone oxime is 52.9%, the ε-caprolactam yield is 48.1% (selectivity: 91.0%). The catalyst turnover (TON) of the ε-caprolactam produced based on phosphorus pentoxide was 13.8 (mol/mol).

EXAMPLES 2 TO 4

The same procedure as in Example 1 was repeated, except that the reaction temperature was changed to 80° C., 100° C. or 120° C., to obtain the results shown in Table I in which the results in Example 1 are also shown.

TABLE 1

| Example No. | Reaction temp. (°C.) | Lactam yield (%) | Lactam selectivity (%) | TON (mol/mol) |
|---|---|---|---|---|
| 1 | 60 | 48.1 | 91.0 | 13.8 |
| 2 | 80 | 64.7 | 91.2 | 18.6 |
| 3 | 100 | 69.1 | 90.1 | 19.8 |
| 4 | 120 | 68.2 | 89.5 | 19.5 |

EXAMPLE 5

In a 200-ml round-bottomed flask purged with nitrogen were placed 75 ml of dried N,N-dimethylformamide and 0.70 g (5.0 mM) of phosphorus pentoxide and the resulting mixture was heated to 95° C. Subsequently, a solution of 8.0 g (70.7 mM) of cyclohexanone oxime in 75 ml of N,N-dimethylformamide was dropwise added to the mixture at 95° C. over 60 minutes, to effect reaction. After completion of the reaction, the reaction mixture was subjected to analysis by a gas chromatography to find that the conversion of cyclohexanone oxime was 100% and the ε-caprolactam yield was 92.1% (selectivity: 92.1%). The catalyst turnover of the ε-caprolactam produced based on phosphorus pentoxide was 13.0 (mol/mol).

EXAMPLES 6 TO 10

In a 200-ml round-bottomed flask purged with nitrogen were placed 23 ml of one of the N,N-dialkyl amide, N-alkyl cyclic amide and dialkyl sulfoxide shown in Table 2 and 0.35 g (2.5 mM) of phosphorus pentoxide, and the resulting mixture was heated to 95° C. Subsequently, a solution of 4.0 g (35.4 mM) of cyclohexanone oxime in 22 ml of an N,N-dialkyl amide solvent as shown in Table 2 was dropwise added to the mixture at 95° C. over 60 minutes to effect reaction. After completion of the reaction, the reaction mixture was subjected to analysis by a gas chromatography to obtain the results shown in Table 2.

TABLE 2

| Example No. | Solvent | Lactam yield (%) | Lactam selectivity (%) | TON (mol/mol) |
|---|---|---|---|---|
| 6 | N,N-diethylformamide | 54.0 | 81.2 | 7.6 |
| 7 | N,N-diisopropylformamide | 32.8 | 64.4 | 4.6 |
| 8 | N,N-dimethylacetamide | 46.2 | 74.3 | 6.5 |
| 9 | Dimethyl sulfoxide | 37.7 | 61.5 | 2.7 |
| 10 | N-methyl-2-pyrrolidone | 27.1 | 57.1 | 3.8 |

EXAMPLES 11 TO 13

In a 200-ml round-bottomed flask purged with nitrogen were placed 23 ml of dried N,N-dimethylformamide and 0.18 g (1.25 mM) of phosphorus pentoxide, and the resulting mixture was heated to 120° C. Subsequently, a solution of 35.5 mM of one of the ketone oximes shown in Table 3 in 22 ml of N,N-dimethylformamide was dropwise added to the mixture at 120° C. over 30 minutes to effect reaction. After completion of the reaction, the reaction mixture was subjected to analysis by a gas chromatography to obtain the results shown in Table 3.

TABLE 3

| Example No. | Starting oxime | Amide product | Yield (%) |
|---|---|---|---|
| 11 | Acetone oxime | N-methylacetamide | 5.6 |
| 12 | syn-Acetophenone oxime | Acetanilide | 12.6 |
| 13 | Cyclopentanone oxime | 2-Piperidone | 10.9 |

EXAMPLES 14 TO 22

A 200-ml, round-bottomed flask purged with nitrogen were placed 45 ml of dried N,N-dimethylformamide, 0.175 g (1.25 mM) of phosphorous pentoxide, and one of the fluorine-containing strong acids and derivatives thereof shown in Table 4, and the resulting mixture was heated to 120° C. Subsequently, a solution of 8.0 g (70.7 mM) of cyclohexanone oxime in 45 ml of N,N-dimethylformamide was dropwise added to the mixture to effect reaction. After completion of the reaction, the reaction mixture was treated with an alkali and then subjected to analysis by a gas chromatography to obtain the results shown in Table 4.

TABLE 4

| | Fluorine-containing strong acid or its derivative | | $\epsilon$-Caprolactam | | |
|---|---|---|---|---|---|
| Example No. | Kind | Amount (mM) | Yield (%) | Selectivity (%) | TON (mol/mol) |
| 14 | $(CF_3SO_2)_2O$ | 0.625 | 58.7 | 91.3 | 32.7 |
| 15 | $CF_3SO_3SiMe_3$ | 0.625 | 47.8 | 92.8 | 24.7 |
| 16 | $CF_3SO_3Et$ | 0.625 | 39.4 | 92.4 | 22.0 |
| 17 | $(CF_3CO)_2O$ | 0.625 | 40.2 | 85.7 | 22.4 |
| 18 | $(CF_3SO_2)_2O$ | 1.25 | 72.1 | 87.5 | 41.0 |
| 19 | $(CF_3SO_2)_2Sn$ | 1.25 | 41.4 | 92.6 | 23.1 |
| 20 | $CF_3SO_3H$ | 1.25 | 54.0 | 92.8 | 30.1 |
| 21 | $(CF_3CO)_2O$ | 1.25 | 48.0 | 90.8 | 26.8 |
| 22 | $BF_3$-ether complex | 1.25 | 55.4 | 90.2 | 30.9 |

COMPARATIVE EXAMPLE 1

The same procedure as in Example 20 was repeated, except that the phosphorus pentoxide was not added. The results obtained were such that the yield of $\epsilon$-caprolactam was 2.0% and the selectivity was 40.2%.

EXAMPLES 23 TO 26

A 200-ml, round-bottomed flask purged with nitrogen were placed 45 ml of dried N,N-dimethylformamide, 1.25 mM of trifluoromethanesulfonic acid anhydride and phosphorus pentoxide in an amount as shown in Table 5, and the resulting mixture was heated to 120° C. Subsequently, a solution of 8.0 g (70.7 mM) of cyclohexanone oxime in 45 ml of N,N-dimethylformamide was dropwise added to the mixture at 120° C. over 30 minutes to effect reaction. After completion of the reaction, the reaction mixture was treated with an alkali and then subjected to analysis by a gas chromatography to obtain the results shown in Table 5.

COMPARATIVE EXAMPLE 2

The same procedure as in Example 23 was repeated, except that the phosphorus pentoxide was not added, to obtain the results shown in Table 5.

TABLE 5

| | | $\epsilon$-Caprolactam | | |
|---|---|---|---|---|
| | Amount of $P_2O_5$ added (mM) | Yield (%) | Selectivity (%) | TON (mol/mol) |
| Example 23 | 0.31 | 45.1 | 93.4 | 113.2 |
| Example 24 | 0.63 | 66.6 | 89.3 | 75.6 |
| Example 25 | 1.25 | 72.1 | 87.5 | 41.0 |
| Example 26 | 2.50 | 85.7 | 90.8 | 24.6 |
| Comp. Example 2 | 0 | 9.2 | 84.3 | — |

EXAMPLES 27 TO 30

In a 200-ml, round-bottomed flask purged with nitrogen were placed 45 ml of dried N,N-dimethylformamide, 0.175 g (1.25 mM) of phosphorus pentoxide and trifluoromethanesulfonic acid in an amount as shown in Table 6, and the resulting mixture was heated to 120° C. Subsequently, a solution of 8.0 g (70.7 mM) of cyclohexanone oxime in 45 ml of N,N-dimethylformamide was dropwise added to the mixture at 120° C. over 30 minutes to effect reaction. After completion of the reaction, the reaction mixture was treated with an alkali and subjected to analysis by a gas chromatography to obtain the results shown in Table 6.

TABLE 6

| | Amount of | $\epsilon$-Caprolactam | | |
|---|---|---|---|---|
| Example No. | $CF_3SO_3H$ added (mM) | Yield (%) | Selectivity (%) | TON (mol/mol) |
| 27 | 1.25 | 54.0 | 92.8 | 30.1 |
| 28 | 2.50 | 71.4 | 92.1 | 39.8 |
| 29 | 3.75 | 78.7 | 92.2 | 43.9 |
| 30 | 5.00 | 88.4 | 93.3 | 49.3 |

EXAMPLES 31 TO 33

In a 200-ml, round-bottomed flask purged with nitrogen were placed 23 ml of dried N,N-dimethylformamide, 0.18 g (1.25 mM) of phosphorus pentoxide and 1.25 mM of trifluoromethanesulfonic acid anhydride, and the resulting mixture was heated to 120° C. Subsequently, a solution of 35.5 mM of one of the ketone oximes shown in Table 7 in 22 ml of N,N-dimethylformamide was dropwise added to the mixture at 120° C. over 30 minutes to effect reaction. After completion of the reaction, the reaction mixture was treated with an alkali and subjected to analysis by a gas chromatography to obtain the results shown in Table 7.

TABLE 7

| Example No. | Starting oxime | Product Amide | Yield (%) |
|---|---|---|---|
| 31 | Acetone oxime | N-methylacetamide | 100 |
| 32 | syn-Acetophenone | Acetanilide | 22.4 |
| 33 | Cyclopentanone oxime | 2-Piperidone | 59.5 |

EXAMPLES 34 TO 37

In a 200-ml, round-bottomed flask purged with nitrogen were placed 90 ml of dried N,N-dimethylformamide, 0.36 g (2.50 mM) of phosphorus pentoxide and 2.50 mm of trifluoromethanesulfonic acid anhydride, and the resulting mixture was heated to a temperature as shown in Table 8. Subsequently, a solution of 16 g (141.4 mM) of cyclohexanone oxime in 90 ml of N,N-dimethylformamide was dropwise added to the mixture at a temperature as shown in Table 8 over 30 minutes to effect reaction. After completion of the reaction, the reaction mixture was treated with an alkali and subjected to analysis by a gas chromatography to obtain the results shown in Table 8.

TABLE 8

| Example No. | Reaction temperature (°C.) | ε-Caprolactam Yield (%) | selectivity (%) | TON (mol/mol) |
|---|---|---|---|---|
| 34 | 60 | 53.5 | 94.4 | 30.7 |
| 35 | 80 | 77.4 | 93.2 | 44.4 |
| 36 | 100 | 75.2 | 91.8 | 43.1 |
| 37 | 120 | 71.5 | 89.0 | 40.1 |

EXAMPLE 38

The same procedure as in Example 36 was repeated, except that the trifluoromethanesulfonic acid anhydride was replaced by antimony pentafluoride. As a result, the ε-caprolactam yield was 57.3%, the selectivity was 91.0% and the catalyst turnover (TON) was 32.9 mol/mol.

What is claim is:

1. A process for producing an amide which comprises subjecting an oxime selected from the group consisting of cyclohexanone oxime, cyclopentanone oxime, cyclododecanone oxime, acetone oxime, 2-butanone oxime, acetophenone oxime and benzophenone oxime to liquid phase rearrangement in the presence of 0.1-50 mole % of phosphorus pentoxide based on the molar amount of the oxime and at least one compound selected from the group consisting of N,N-dialkyl amides, N-alkyl cyclic amides and dialkyl sulfoxides.

2. A process for producing an amide which comprises subjecting an oxime selected from the group consisting of cyclohexanone oxime, cyclopentanone oxime, cyclododecanone oxime, acetone oxime, 2-butanone oxime, acetophenone oxime and benzophenone oxime to liquid phase rearrangement in the presence of a fluorine-containing strong acid or its derivative, 0.01-50 mole % of phosphorus pentoxide based on the molar amount of the oxime and at least one compound selected from the group consisting of N,N-dialkyl amides, N-alkyl cyclic amides and dialkyl sulfoxides, wherein the amount of the fluorine-containing strong acid or its derivative is 0.1-50 moles per mole of the phosphorus pentoxide.

3. The process according to claim 1, wherein the N,N-dialkyl amides include N,N-dimethylformamide, N,N-diethylformamide, N,N-diisopropylformamide, N,N-dibutylformamide, N,N-dihexylformamide, N,N-dimethylacetamide, N,N-diethylacetamide, N,N-diisopropylacetamide, N,N-dimethylpropionamide, N,N-dimethylbutyramide and N,N-dimethylcapronamide.

4. The process according to claim 2, wherein the N,N-dialkyl amides include N,N-dimethylformamide, N,N-diethylformamide, N,N-diisopropylformamide, N,N-dibutylformamide, N,N-dihexylformamide, N,N-dimethylacetamide, N,N-diethylacetamide, N,N-diisopropylacetamide, N,N-dimethylpropionamide, N,N-dimethylbutyramide and N,N-dimethylcapronamide.

5. The process according to claim 1, wherein the N-alkyl cyclic amides include N-methylpyrrolidone and N-methylpiperidone.

6. The process according to claim 2, wherein the N-alkyl cyclic amides include N-methylpyrrolidone and N-methylpiperidone.

7. The process according to claim 1, wherein the dialkyl sulfoxides include dimethylsulfoxide, diethylsulfoxide, dipropylsulfoxide and dihexylsulfoxide.

8. The process according to claim 2, wherein the fluorine-containing strong acid or its derivative is selected from the group consisting of trifluoromethanesulfonic acid, trifluoromethanesulfonic acid anhydride, ethyl trifluoromethanesulfonate, trimethylsilyl trifluoromethanesulfonate, tin trifluoromethanesulfonate, trifluoroacetic acid, trifluoroacetic acid anhydride, boron trifluoride, boron trifluoride-ether complex and antimony pentafluoride.

9. The process according to claim 1, wherein the N,N-dialkyl amides are $C_{1-6}$ carboxylic acid amides each having two same or different alkyl groups on its nitrogen atom, said alkyl groups each having 1 to 6 carbon atoms; the N-alkyl cyclic amides are cyclic amides each having 4 to 6 carbon atoms and having an alkyl group having 1 to 6 carbon atoms on its nitrogen atom; and the dialkyl sulfoxides are sulfoxides having two same or different alkyl groups each having 1 to 6 carbon atoms.

10. The process according to claim 2, wherein the N,N-dialkyl amides are $C_{1-6}$ carboxylic acid amides each having two same or different alkyl groups on its nitrogen atom, said alkyl groups each having 1 to 6 carbon atoms; the N-alkyl cyclic amides are cyclic amides each having 4 to 6 carbon atoms and having an alkyl group having 1 to 6 carbon atoms on its nitrogen atom; and the dialkyl sulfoxides are sulfoxides having two same or different alkyl groups each having 1 to 6 carbon atoms.

11. The process according to claim 1, wherein the oxime is cyclohexanone oxime.

12. The process according to claim 2, wherein the oxime is cyclohexanone oxime.

13. The process according to claim 1, wherein the rearrangement is effected at a temperature of about 20°-200° C.

14. The process according to claim 2, wherein the rearrangement is effected at a temperature of about 20°-200° C.

* * * * *